US009782064B1

(12) United States Patent
Linder et al.

(10) Patent No.: US 9,782,064 B1
(45) Date of Patent: Oct. 10, 2017

(54) OBTAINING AND DISPLAYING HISTOGRAM AND/OR CONFIDENCE OF INTRA-OPERATIVE REFRACTION AND/OR IOL POWER RECOMMENDATION

(71) Applicant: CLARITY MEDICAL SYSTEMS, INC., Pleasanton, CA (US)

(72) Inventors: Barry Linder, Danville, CA (US); Yan Zhou, Pleasanton, CA (US); Bradford Chew, San Ramon, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 0 days.

(21) Appl. No.: 15/094,169

(22) Filed: Apr. 8, 2016

(51) Int. Cl.
A61B 3/14 (2006.01)
A61B 3/00 (2006.01)
A61B 3/10 (2006.01)
A61B 3/15 (2006.01)

(52) U.S. Cl.
CPC .......... *A61B 3/0025* (2013.01); *A61B 3/0058* (2013.01); *A61B 3/1015* (2013.01); *A61B 3/152* (2013.01)

(58) Field of Classification Search
CPC ..... A61B 3/0025; A61B 3/0058; A61B 3/152; A61B 3/1015
USPC ................................. 351/208, 206, 205, 200
See application file for complete search history.

(56) References Cited

U.S. PATENT DOCUMENTS

| 6,637,884 B2 * | 10/2003 | Martino ............... A61B 3/1015 |
| | | 351/212 |
| 7,130,835 B2 | 10/2006 | Cox et al. |
| 7,708,411 B2 | 5/2010 | Polland et al. |
| 8,356,900 B2 | 1/2013 | Zhou et al. |
| 8,678,591 B2 | 3/2014 | Zhou et al. |
| 8,820,929 B2 | 9/2014 | Shea et al. |
| 8,857,985 B2 | 10/2014 | Zhou et al. |
| 8,882,270 B2 | 11/2014 | Zhou et al. |
| 8,919,957 B2 | 12/2014 | Zhou et al. |
| 8,919,958 B2 | 12/2014 | Zhou et al. |
| 9,039,181 B2 | 5/2015 | Zhou et al. |
| 9,050,026 B2 | 6/2015 | Zhou et al. |
| 9,101,292 B2 | 8/2015 | Zhou et al. |
| 9,107,608 B2 | 8/2015 | Zhou et al. |
| 9,113,819 B2 | 8/2015 | Zhou et al. |

OTHER PUBLICATIONS

Krueger, et al., "Intraoperative, real-time aberrometry during refractive cataract surgery with a sequentially shifting wavefront device. J Refract Surg." 2013; vol. 29, pp. 630-635.

(Continued)

*Primary Examiner* — Tuyen Tra
(74) *Attorney, Agent, or Firm* — Kilpatrick Townsend & Stockton LLP

(57) ABSTRACT

In order to take advantage of the real time nature of intra-operative refraction or wavefront aberrometry, and visually make the history of the measurements apparent to a surgeon, a histogram of frequency vs IOL results calculated from an IOL formula is computed and IOL suggestions being accumulated are displayed in a histogram. One embodiment is a means to present to a surgeon a histogram of intra-operative refractions. Another embodiment is to automatically and intra-operatively detect the aphakic phase of a cataract surgery to display a histogram of a recommended IOL power.

15 Claims, 8 Drawing Sheets

(56) References Cited

OTHER PUBLICATIONS

Ianchuley, T, Hoffer KJ, Yoo SH, Chang DF, Breen M, Padrick T, Tran DB. Intraoperative refractive biometry for predicting intraocular lens power calculation after prior myopic refractive surgery. Ophthalmology. 2014;121:56-60.

* cited by examiner

OBTAINING AND DISPLAYING HISTOGRAM AND/OR CONFIDENCE OF INTRA-OPERATIVE REFRACTION AND/OR IOL POWER RECOMMENDATION

TECHNICAL FIELD OF THE INVENTION

One or more embodiments of the present invention relate generally to intra-operative refraction or wavefront aberrometry. In particular, one embodiment is related to means to present to a surgeon the histogram and/or confidence level of intra-operative refraction or wavefront aberrometry measurement during a cataract surgery, especially the histogram, and/or confidence level of aphakic refraction and/or the associated intra-ocular lens (IOL) power recommendation.

BACKGROUND OF THE INVENTION

A need has been identified in recent years in terms of providing real time intra-operative refraction or wavefront measurement feedback to a surgeon performing a refractive cataract surgery or other vision correction procedures on the eye of a patient. The intra-operative refraction or wavefront measurement, especially one obtained from an aphakic eye when the natural lens of the eye is removed, can help to guide a surgeon better determine the optical power of an IOL (intra-ocular lens) (in terms of sphere power for a monofocal or multi-focal or extended depth of focus IOL or accommodating IOL, and cylinder in addition to sphere if the IOL is a toric IOL or even higher order aberration correction if it is a premium higher order correction IOL). Such an approach has been shown to produce better surgical outcomes. Meanwhile, an intra-operative pseudo-phakic refraction or wavefront measurement can also confirm if a targeted refraction has been achieved to within a certain acceptable tolerance and if not, further adjustment (such as a further rotation of an implanted toric IOL or limbal relaxing incision) can be made to finely tune the refraction.

However, one issue associated with the use of an intra-operative wavefront aberrometer or auto-refractor is that the real time refraction value can vary as a result of many dynamic surgical factors, including the alignment of the patient eye relative to the aberrometer or auto-refractor, patient fixation and angle alpha (angle between the center of the pupil and the visual axis), varying pupil size, the intra-ocular pressure (IOP), the hydration of the incision wound, the tear film, and the pressure exerted on the cornea from eye-lid-opening speculum. With proper control of these dynamic surgical factors and artificial intelligence including refraction confidence calculation to qualify and hence reject disqualified refraction/wavefront data, the variation in the measured refraction can be controlled to a certain range. However, there can still be some variation in the measured refraction when a patient eye is aligned relative to the intra-operative aberrometer or auto-refractor. This is more the case when an eye is aphakic, as an aphakic eye generally has a larger absolute base sphere refraction value simply because the wavefront from an aphakic eye is more divergent than that from an emmetropic eye. As a result, the recommended intra-ocular lens (IOL) power based on the real time aphakic refraction (combined with other biometric parameters) can also change in real time, for example, when the eye is re-aligned. This can cause some confusion to a surgeon in determining what exact IOL power to select for implantation during a cataract surgery.

In light of the above, there is a need in the art for a means to show a surgeon how repeatable a refraction reading is and/or how confident the refraction is. In the aphakic state, this will allow the surgeon to make a more informed decision in terms of selecting a recommended IOL power and in the pseudo-phakic state, this will allow the surgeon to finely tune the final position of an implanted IOL until with higher confidence.

One or more embodiments of the present disclosure satisfy one or more of the above-identified needs in the art. One embodiment is a means to present to a surgeon a histogram of real time refractions at each stage of a refractive cataract surgery, i.e. phakia, aphakia and pseudo-phakia. Another embodiment is to automatically and intra-operatively detect the phase of a cataract surgery (i.e. to intra-operatively determine if a patient eye is phakic, aphakic, or pseudo-phakic). Another embodiment is to display a real-time, dynamic histogram of a recommended IOL power calculated from aphakic refractions together with other biometric parameters of the eye.

One aspect of the present disclosure is to record the occurrence frequency of qualified and/or rounded real time refractions and to display the occurrence frequency distribution or histogram of the refraction data. This will present to the surgeon an information rich display of quantitative refraction instead of a most recently single qualified refraction at one point in time, which may be more variable. Another aspect of the present disclosure is to use phakic biometry measurement results of an eye obtained either pre-operatively or intra-operatively to estimate its aphakic refraction, to use an estimated aphakic refraction to automatically detect the aphakic phase of the eye. Still another aspect is to use intra-operative biometry measurement to determine the cataract surgical phase of an eye. Still another aspect is to use intra-operative Purkinje images to determine the cataract surgical phase of an eye. Still another aspect is to combine real time aphakic refraction with phakic and/or aphakic biometry to calculate an IOL power per a targeted final refraction and to present to a surgeon a dynamic histogram of the IOL power recommendations during the aphakic phase. Still another aspect is to optimize and personalize the IOL power calculation in a regression manner by collecting data over a relatively large number of patients for each surgeon to account for surgeon factors.

Another embodiment of the present disclosure is to display the confidence level of real time intra-operative refraction. One aspect is to calculate a confidence level or value based on an algorithm that takes into account all wavefront and/or aberrometry data qualifiers and to present to a surgeon the confidence level or value as a height or length varying percentage bar. Another aspect is to correlate the confidence percentage value to a color encoded confidence percentage indicator (such as the word "Rx"). In this case, the confidence value can be digitized such that for a certain real time refraction that falls within a certain digitized confidence value range, a certain color selected from a color spectrum is assigned to the real time refraction and is displayed to the surgeon.

Still another embodiment of the disclosure is to combine the calculation of the occurrence frequency or probability distribution of qualified refraction with the confidence level of the refraction to produce a combined confidence weighted histogram and to present this confidence weighted histogram to a surgeon in real time. One aspect is to use the confidence weighted histogram to pick the most steady aphakic refraction, and to use the chosen aphakic refraction to calculate the IOL power. Another aspect is to allow the surgeon the option to display only the refraction histogram and/or the refraction confidence bar and/or the combined confidence weighted refraction histogram to guide the surgery. In particular, at the aphakic phase, the surgeon can select the IOL power based on the live, dynamic IOL power histogram; and at the pseudo-phakic phase, the surgeon can use the live refraction histogram to rotate an implanted toric IOL or to perform a guided limbal relaxing incision.

DETAILED DESCRIPTION

Intra-operative refraction of a patient eye (or alternatively, a subject eye) undergoing a refractive cataract surgery using an intra-operative refraction measurement device such as a wavefront aberrometer or auto-refractor has been shown to improve the refractive surgical outcome. Traditionally, ophthalmic refraction measurements are done in a snap-shot or single measurement manner (although such a single measurement can involve the averaging of a number of snap shots of measurements). When such a measurement is transferred to intra-operative refraction of a patient eye undergoing a refractive cataract surgery, it tends to hide the variability of the measurement result as the refraction of an eye undergoing a surgery is dependent on a number of dynamic surgical factors, including the alignment of the eye relative to the intra-operative refraction device, the condition of the cornea as well as the condition of the anterior chamber of the eye. In fact, even with the use of a snap-shot refraction measurement device, when a surgeon (or other operator) does multiple intra-operative measurements, the refraction measurement results will most likely vary and this variation can cause confusion to a cataract surgeon, especially if the surgeon relies on aphakic intra-operative refraction to determine the IOL power to be selected. Such variability in the pseudo-phakic phase can also cause confusion to a surgeon if the surgeon relies on intra-operative pseudo-phakic refraction to determine the position of an implanted IOL such as the orientation axis of a toric IOL or the amount of limbal relax incision to neutralize astigmatism. The variability of intra-operative refraction became more evident after real time intra-operative wavefront aberrometers were introduced to the refractive cataract surgery practice.

Figure 1:
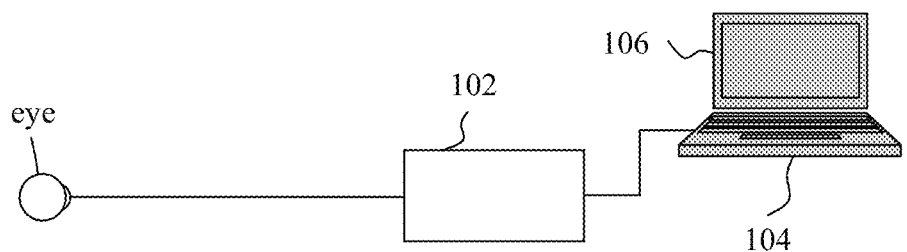
FIG. 1 shows a schematic diagram of an embodiment system comprising an intra-operative eye refraction measurement device, a digital processor and a display.

In accordance with one embodiment of the present disclosure, a real time eye refraction measurement device is coupled to a digital processor and a display. FIG. 1 shows a schematic diagram of such an embodiment, in which a real time intra-operative eye refraction measurement device such as a wavefront sensor or an auto-refractor 102 is coupled to a digital processor 104 and is linked to a display 106. The digital processor 104 is configured to capture/record intra-operative refraction (or wavefront measurement) and to process the refraction or wavefront data in real time to qualify the data and to reject disqualified data.

The qualification of the real time data can be based on various qualification parameters or qualifiers. One important qualifier is the alignment of a patient eye relative to the refraction measurement device. From a practical point of view, for example, when an eye is aligned to within ±0.1 mm of the refraction measurement device optical axis, the alignment can be considered very good and when the eye is aligned to within ±0.5 mm of the device optical axis, the alignment can be considered still acceptable. Therefore, a threshold of ±0.5 mm can be established as the pass/fail criterion for qualifying or disqualifying the data in terms of eye alignment relative to the refraction measurement device.

Another important qualifier is the uniformity of optical power or energy among different sampled sub-wavefronts. A uniformity ratio can be defined as the relative standard deviation of optical energy or power among different sampled sub-wavefronts, i.e. as standard deviation divided by the average value. As an example, the uniformity ratio threshold can be 6%. The data qualification process will therefore reject any refraction frame data that has a uniformity ratio greater than the threshold. Alternatively, the uniformity qualification parameter can also be defined as an occlusion parameter which is the maximum minus minimum value divided by the average in terms of optical energy or power among different sampled sub-wavefronts. An associated threshold (such as three times that of the uniformity ratio) can also be defined to qualify the refraction data. Note that this qualification process will likely remove data associated with surgical factors that partially block the overall wavefront light beam or reflect the incident light probe beam that travels to a patient eye to create the returned wavefront beam. These surgical factors can include, for example, a surgical tool positioned in the probe beam path, thus reflecting the probe beam back to the refraction measurement device; a surgical tool positioned in the wavefront beam path that partially block and hence attenuate light related to some sub-wavefronts; an air bubble or cortex leftovers inside the anterior chamber or the lens capsule of a patient eye that either absorb(s) or scatter(s) light related to some sub-wavefronts; a blob or puddle of visco-elastic material or irrigation solution left on the cornea of a patient eye that directs away light related to some sub-wavefronts.

Another qualifier is the amount or degree of higher order aberrations. This qualifier can be considered as how good the overall aberrations fit as sphere and cylinder refractive errors. If the fitting is not good, we can consider the overall wavefront as more departed from being characterized as a pure combination of sphere and cylinder refractive errors. The degree of departure of the overall wavefront from a combination of sphere and cylinder refractive errors can be defined as the square root of the summation of the square of the distance of each data point from its expected position on an ellipse that represents a combination of sphere and cylinder. A threshold can be established such that if the degree of departure is above the threshold, the wavefront data will be disqualified. Factors that can increase this qualification value include a surgical tool partially blocking the wavefront, keratoconus, scars on a cornea, air bubbles or cortex leftovers inside an eye, visco-elastic gel on a cornea, and irrigation event.

Still another qualifier is the average prismatic tilt of the overall wavefront. For example, if the averaged overall wavefront tilt is pointing at an angle within 1 degree from the optical axis of the eye refraction measurement device, the prismatic tilt of the overall wavefront can be considered very highly qualified. A threshold of, for example, 11 degree can be set and if one finds that the averaged overall wavefront tilt is pointing at an angle greater than the threshold, the wavefront data can be disqualified.

Still another qualifier is the overall signal strength of the wavefront. If there is no eye under the refraction measurement device, for example, when the device is sending the probe beam directly to the floor of an OR (operating room), the wavefront signal returned from the floor will generally be much weaker than that from a real eye. A signal strength range can therefore be defined that covers the full range over all phases and all pigmentation eyes. When the returned wavefront signal strength is outside this pre-defined range, the data will be disqualified.

Still another qualifier is the steadiness of the wavefront data from one frame to the next. In a transient situation such as the movement of a patient eye, the disturbance of the wavefront by an irrigation event, or the movement of a surgical tool within the wavefront path, the wavefront data received may not be steady, i.e. measured refraction changing more than desired from frame to frame. A threshold can be established to require that the change in the sphere and cylinder value from one frame to the next need to be no more than, for example, ±0.5 diopter. If the change is more than this threshold, the data from both frames will be disqualified.

Note that there can be more qualification parameters. In addition to the qualification of the wavefront data, the digital processor 104 can also be further configured to process the qualified data to produce a real time dynamic histogram of the intra-operative refraction (or wavefront measurement) and to display such a histogram on the display. As time goes on during a particular phase of a cataract surgery (such as the aphakic phase), the histogram will also be updated in real time to reflect how steady a measured refraction with a high occurrence frequency gradually becomes.

As an option, the digital processor 104 can also be configured to digitize the qualified refraction data, for example, in quarter diopter steps, to further limit small variations of the live refraction within a quarter diopter to the same value.

By displaying such a histogram to a surgeon in real time during a cataract surgery, the surgeon can know which refraction value is produced most often by the intra-operative refraction measurement device and hence use that value as the more likely "true" refraction of the patient eye in that surgery phase.

In addition, the digital processor 104 can also be configured to automatically recognize the qualified refraction that has the highest occurrence frequency and directly present this refraction to the surgeon. It can be understood that this refraction may change as the cataract surgery initially enters a phase and will gradually stabilize once the eye is properly prepared and conditioned for refraction measurement and is aligned to the refraction measurement device 102 for a certain alignment holding time. With practice, a surgeon will figure out a reasonable holding time to enable the refraction having the highest occurrence frequency to stabilize.

As an option, the time length for the refraction that will be used to produce the histogram can also be pre-defined such that older qualified refraction data are automatically removed while more current new qualified data are added. The time length can also be personalized for a particular surgeon and be limited to a reasonable and practical value. For example, the time length can be 3 seconds to 10 seconds, during which a surgeon can normally keep the eye position of a patient aligned for a reasonably "reliable" high occurrence frequency refraction to be displayed.

Figure 2:
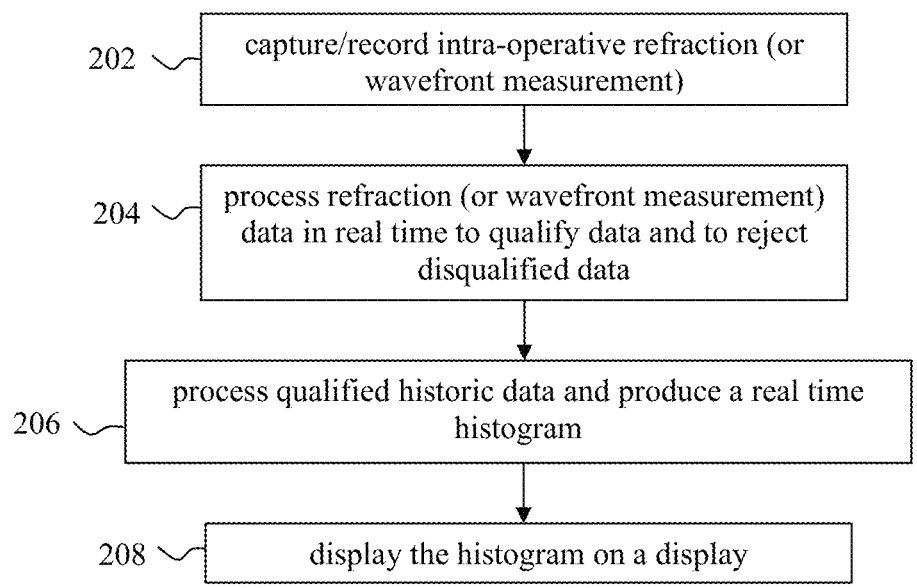
FIG. 2 shows the major steps involved in the presently disclosed means to provide a surgeon the histogram of live refraction.

FIG. 2 shows the major steps involved in one embodiment to obtain and present to a surgeon the histogram of live intra-operative refraction. The first step 202 is to capture/record intra-operative refraction or wavefront data. The second step 204 is to process the refraction or wavefront data to reject disqualified data. The third step 206 is to process the qualified historic data and to produce a real time histogram. The fourth step 208 is to display a live refraction histogram on a display.

As an option, instead of displaying the histogram that contains all the qualified refraction values, the last step can be to display digitized refraction that has the highest occurrence frequency or to display only a few digitized refraction values including the one that has the highest occurrence frequency as well as a few surrounding ones (such as one or two on each side) that have occurrence frequencies next to the highest occurrence frequency.

Alternatively and more advantageously, as another embodiment of the present disclosure, instead of being configured to display a continuously updated histogram of real time refraction, the digital processor can be configured to combine the qualified aphakic refraction data with biometric data of the eye obtained either pre-operatively or intra-operatively to calculate a recommended IOL power, to produce a live dynamic histogram of the IOL power recommendation, and to display such a histogram on a display. This will be especially beneficial to a surgeon in terms of helping the surgeon to determine which recommended IOL power to choose for implantation. In general, the recommended IOL power will change as an aphakic eye is initially prepared and aligned to the intra-operative refraction measurement device 102 and the recommended IOL power will stabilized as the aphakic eye is held aligned longer. In practice, after a surgeon has prepared and conditioned an aphakic eye, he/she can align the patient eye and hold the patient head steady for a certain time (for example 3 to 5 seconds) to get a relatively steady recommended IOL power that has the highest occurrence frequency. The surgeon can then select this recommended IOL power or compare this IOL power with that based purely on pre-operative biometry data and select a value of his/her choice such as a value in between these two values.

It should be understood that the term biometric data of an eye can include all anatomical parameters of an eye that can be measured either pre-operatively or intra-operatively. In practice, these parameters can be measured optically and ultrasonically and they include axial length, anterior chamber depth, corneal anterior (K or keratometry values) and posterior profiles, corneal steep meridian and flat meridian axis and power, corneal astigmatism, cornea thickness, aqueous depth, lens thickness, lens anterior and posterior profile, pupil size or diameter, pupil center, white to white distance, iris center, and retina thickness, etc.

The reason why these parameters can be combined with aphakic refraction to better predict an IOL is that without aphakic refraction, one can only indirectly calculate and hence predict the optical power of the cornea using for example, a keratometer or corneal topographer or an OCT or a Pentacam. With aphakic refraction, the optical power of the cornea (in both sphere and cylinder) can be directly measured with higher accuracy. Once the cornea optical power, the axial length of an eye and a targeted final refraction is determined, and the final effective lens position of the IOL is predicted, the IOL power can be calculated. In terms of predicting the effective lens position of an IOL, the prediction is generally highly dependent on a so called A-constant that reflects the property of haptics or arms of a particular IOL and the lens itself, which is manufacturer dependent. Meanwhile, the effective lens position of an IOL is also dependent on the anatomic parameters of an eye and these anatomic or biometric parameters include the white to white distance, the anterior chamber depth and the lens capsule position. Therefore, a combination of aphakic refraction with pre- or intra-operative biometric measurement can result in a better surgical outcome.

It should be noted that all other features that have been discussed with respect to real time refraction can be transferred to real time IOL power recommendation at the aphakic phase. Meanwhile, at the aphakic phase, one can also either configure the digital processor to produce and display a histogram of real time refraction or configure it to produce and display a histogram of real time IOL power recommendation or even configure it to produce and display both a histogram of real time refraction and a histogram of real time IOL power recommendation.

As in the case of refraction, the digital processor 104 can also be configured to digitize the IOL power calculated based on the qualified refraction data and the pre- or intra-op biometry data. For example, the digitization of IOL power recommendation can be in half diopter steps to further limit small variations of the recommended IOL power within half diopter to the same value. In addition, the digital processor 104 can also be configured to automatically recognize the calculated IOL power that has the highest occurrence frequency and directly present this IOL power to the surgeon.

Similarly, as another option, the time length for calculating the IOL power histogram can also be pre-defined such that older IOL power data are automatically removed while more current new IOL power data are added. Again the time length can be personalized for a particular surgeon and be limited to a reasonable and practical value. For example, the time length can be 3 seconds to 10 seconds, during which a surgeon can normally keep the position of the eye of a patient eye aligned steady for a reasonably "steady" IOL power recommendation having the highest occurrence frequency to be displayed.

Figure 3:
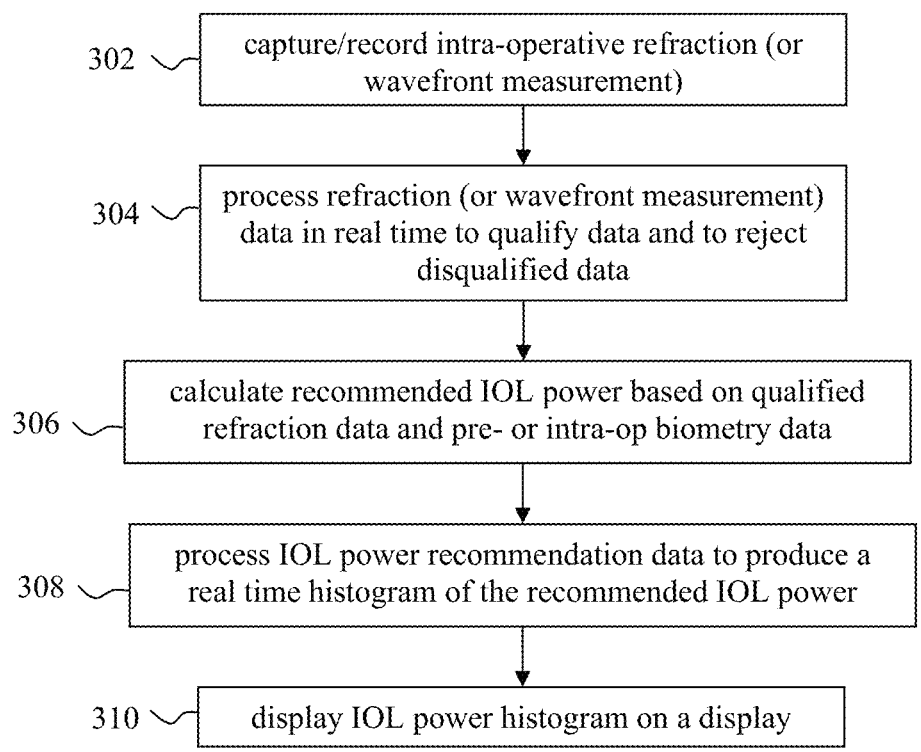
FIG. 3 shows the major steps involved in the presently disclosed means to display the histogram of live IOL power recommendations.

FIG. 3 shows the major steps involved in the presently disclosed means to display the histogram of live IOL power recommendation at the aphakic phase. The first step 302 is to capture/record intra-operative refraction (or wavefront measurement) data. The second step 304 is to process the data in real time to qualify the data and to reject disqualified data. The third step 306 is to calculate a recommended IOL power based on the qualified aphakic refraction data and pre- or intra-op biometry data. The fourth step 308 is to process the IOL power recommendation data to produce a live dynamic histogram of the recommended IOL power. The fifth step 310 is to display such an IOL power histogram on a display.

As in the case of refraction, optionally, instead of displaying the histogram that contains all the IOL power recommendation values, the last step can be to display only a few (such as 3) digitized IOL powers including the one that has the highest occurrence frequency as well as a few surrounding ones (such as 2 with one on each side) that have their occurrence frequencies next to and on both sides of the highest occurrence frequency.

Figure 4:
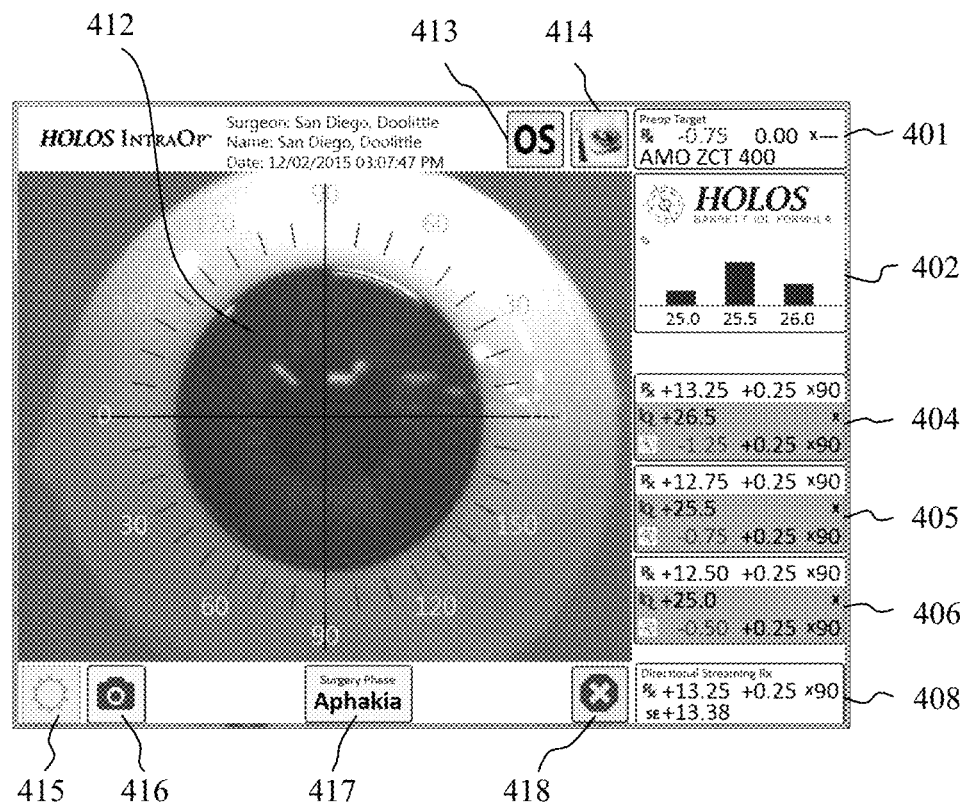
FIG. 4 shows an example display of an IOL power histogram together with some other parameters as well as a live eye image.

FIG. 4 shows an example of such an IOL power histogram display together with some other parameters as well as a live eye image. Note that in the right column of the display, there is an IOL power histogram 402 that shows three digitized IOL power recommendations, i.e. 25.0, 25.5 and 26.0 diopters. Associated with each recommended IOL power is a vertical bar with a height that represents the respective relative occurrence frequency or probability. In this case, the most frequently occurred IOL power recommendation is 25.5 diopter. The next most frequently occurred IOL power recommendation is 26.0 diopter.

In addition, as another embodiment, the total number of measurements/IOL calculations that are included in the histogram can be displayed in real time. Note that this value is not shown in FIG. 4 and it can be shown anywhere on the display, but is preferably shown directly on or next to the histogram.

In FIG. 4, the live display also shows a live eye image 412; which eye 413 (left or right) is being operated, the orientation of the eye 414 relative to the surgeon (temporal or superior), a soft fixation light switch 415 (to turn a blinking fixation light on and off), a soft button 416 for capturing one or more snap shot(s) of the current screen print, the phase of surgery 417 (in this case, aphakia); a soft session start/stop button 418. On the right column, in addition to the histogram 402, there is a box 401 that shows the pre-op targeted refraction and the type of IOL intended to be used for implantation; the three boxes 404, 405 and 406 show the latest three qualified and digitized real time refractions together with their respective corresponding IOL power recommendations and the corresponding expected final pseudo-phakic refractions; the bottom box 408 shows the current real time refraction reading together with its corresponding spherical equivalent (SE). Note that this current real time refraction reading can be qualified with a lower qualification or confidence threshold and the values can be rounded to the 0.01 digit of a diopter.

At this point, a question to ask is how the phase of surgery can be determined intra-operatively to ensure the recommended IOL power makes sense, i.e., the refraction value being used for the calculation of the IOL power needs to be that from the aphakic phase. Note that one feature in this disclosure is to automatically and intra-operatively detect the phase of a cataract surgery.

Figure 5A:
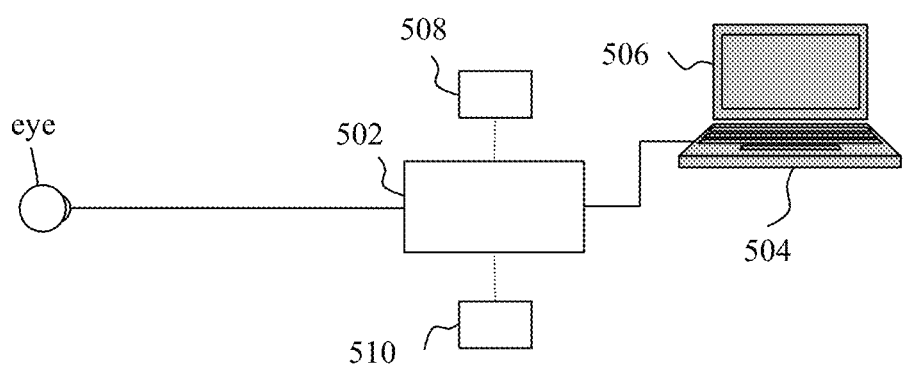
FIG. 5A shows a generic schematic diagram similar to that of FIG. 1 but with the difference in that the intra-operative refraction measurement device can include a camera and/or a biometric parameter measuring sub-module, and the digital processor is configured to automatically detect the phase of the surgery to determine if the eye is phakic or aphakic or pseudo-phakic.

FIG. 5A shows a generic schematic diagram of such a device. Compared to the FIG. 1, the difference is in that the eye refraction measurement device 502 may contain other eye property measurement submodules and the digital processor is configured to use pre- or intra-operative biometric and/or eye image data and real time refraction data to automatically determine the phase of the eye undergoing a cataract surgery, i.e. from phakia, to aphakia and to pseudo-phakia.

It is well known that there is a relatively big change in the average refraction (i.e. spherical equivalent) of an eye from its phakic phase to its aphakic phase, and also mostly likely from its aphakic to its pseudo-phakic phase (except for the case when the eye is extremely long). In fact, if spherical equivalent is used to gauge the difference, the difference in diopter value from a phakic phase to an aphakic phase of the same eye is of the order of about 10 diopters. In one embodiment of the present disclosure, pre- or intra-operative biometry measurement results and/or pre-operative refraction (or wavefront measurement) data are used to determine an expected refraction of the eye in its phakic phase and aphakic phase, and targeted refraction is used to determine expected pseudo-phakic refraction. Once a cataract surgery starts, qualified real time refraction measurement result is consistently compared with the expected refraction of the eye at different phases. If the qualified real time refraction (such as spherical equivalent) is within a certain tolerance range (for example, ±3.0 D or more preferably a range selectable by an end user from ±0.5 D to ±4.0 D) from the expected phakic refraction (such as the pre-op refraction or a calculated phakic refraction using pure eye biometry data or a combination of these data), the state of the eye can be considered as phakic; if the qualified real time refraction is within a certain tolerance range (for example, ±3.0 D, or more preferably a range selectable by an end user from ±0.5 D to ±4.0 D) from the expected aphakic refraction (such as a value calculated using theoretical vergence formula based on axial eye length and corneal power derived from K-measurements), the state of the eye can be considered as aphakic; and finally, if the qualified real time refraction is within a certain tolerance range (for example, ±3.0 D, or more preferably a range selectable by an end user from ±0.5 D to ±4.0 D) from the targeted refraction after the aphakic phase, the state of the eye can be considered as pseudo-phakic.

Note that the reason for choosing the example of ±3.0 D as one preferred tolerance range is that in most cases, temporary surgical factors such as the hydration of incision wound, the change in the intra-ocular pressure, and the pressure exerted on a cornea from a speculum, will not cause the average refraction of the eye to depart from its expected value by more than approximately ±2.0 D.

In some cases like a dense cataract or femto laser cases, either pre-op or intra-op phakic refraction of the eye may be impossible or unreliable due to strong scattering of light by the dense cataract lens or some other strong light scattering regions in the eye such as optical bubbles created by a femto laser. Also, if the eye is extremely long, the difference in refraction between its aphakic phase and its pseudo-phakic phase can be smaller than the tolerance range which can cause an overlap between the expected refraction in the aphakic phase and that in the pseudo-phakic phase. In these cases, using just expected refractions to compare with real time refraction may not be enough to differentiate the phases of a cataract surgery.

As an embodiment, information from real time Purkinje images can be used to help determine the phase. This is because the Purkinje images are very different from one phase to another phase. In fact, the natural lens of an eye is relatively thicker when compared with an artificial intra-ocular lens (IOL) and the refractive index of a natural lens is generally lower than that of an IOL. Therefore, the third and fourth Purkinje images created by the front and back interfaces of a natural lens are less bright and more separated as compared to those of an IOL. Further, in the aphakic phase, due to the fact that there is no natural or artificial lens in the eye, there are only the first and second Purkinje images created by the front and back interfaces of the cornea. In terms of hardware, there is a need for a live eye camera to be associated or coupled to the eye refraction measurement device, and fortunately, this is generally the case as such a camera is needed to guide a surgeon in aligning an eye to the eye refraction measurement device. Note that in FIG. 5A, such a camera 508 is represented by a box linked to the eye refraction measurement device 502 via a dashed line and this camera 508 can be integrated inside the eye refraction measurement device as will be discussed shortly in FIG. 5B.

As still another embodiment, an eye biometric parameter measurement submodule 510 is coupled to or integrated inside the eye refraction measurement device 502. In FIG. 5A this is shown with the box 510 linked by a dashed line to the box 502. The submodule 510 can be an optical coherence tomography (OCT) module or simply an optical low coherence reflectometer (OLCR) as will be discussed shortly in more detail in FIG. 5B. The difference between an OCT and an OLCR is that an OCT can perform two dimensional scanning to obtain a three dimensional volumetric data set of optical reflection/scattering information and an OLCR does not do any transverse scanning so it can only obtain optical reflection/scattering information along a single line. However, in terms of intra-operatively obtaining information on whether there is a natural lens, or no lens or an artificial IOL in an eye, both OCT and OLCR can do the job simply because a phakic natural lens is much thicker with less strong reflection/scattering from its optical interfaces than a pseudo-phakic IOL, and meanwhile in the aphakic phase, there is no lens at all. Both OCT and OLCR can hence detect these conditions. Therefore, the digital processor in FIG. 5A can be configured to use either OCT or OLCR obtained information to determine the phase of a cataract surgery.

Note that even though either an OCT or an OLCR can provide the information on the phase of the eye under a cataract surgery, an OCT is preferred because it can also provide information on other anatomic or biometric parameters which is useful in calculating the IOL power as we discussed before.

Figure 5B:
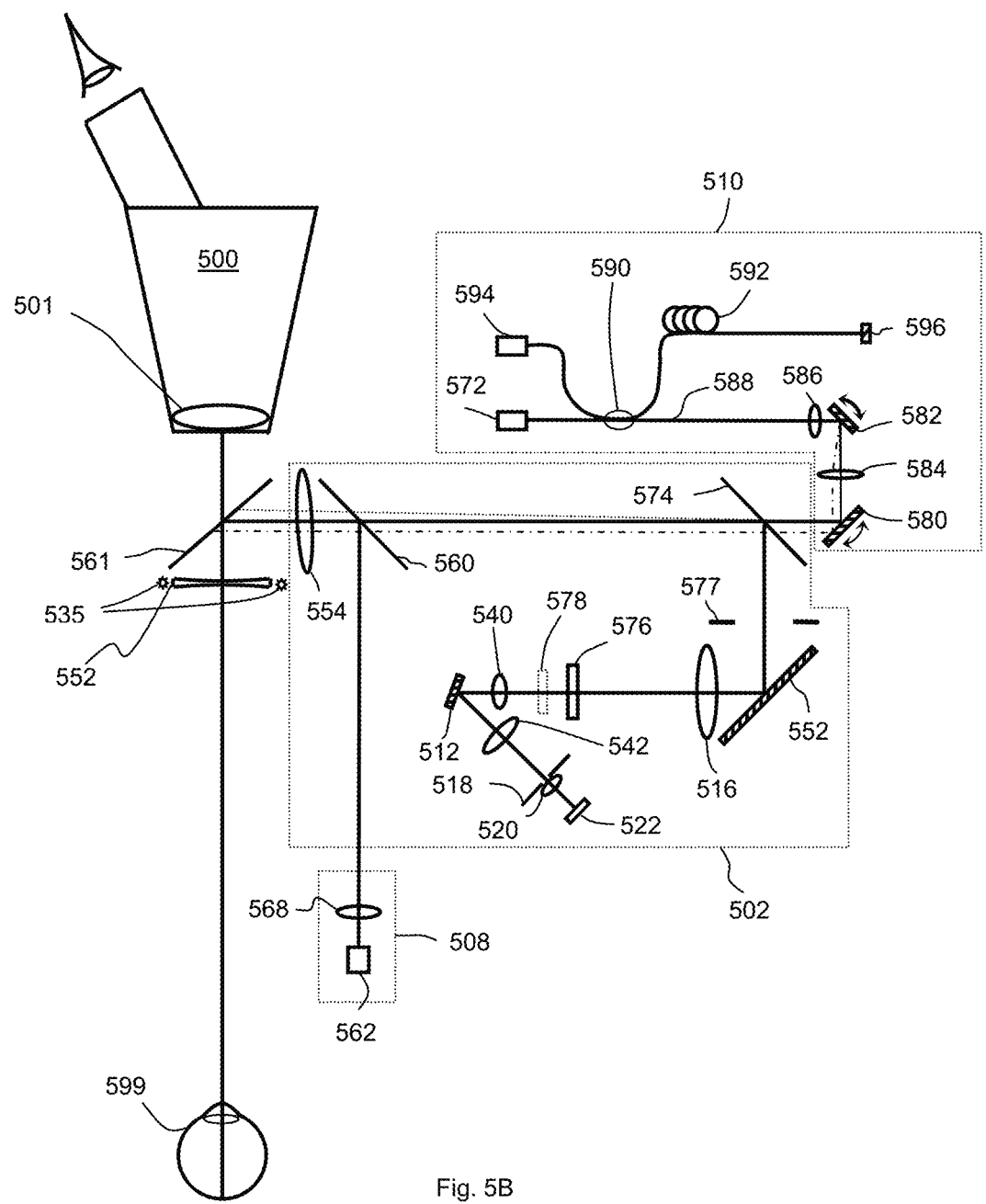
FIG. 5B shows an embodiment in which a sequential wavefront sensor is integrated with an eye camera and an optical coherence based biometric parameter measurement submodule.

To illustrate a more specific embodiment, FIG. 5B shows a schematic diagram in which a sequential wavefront sensor is integrated with an eye camera and an optical coherence tomographer (OCT) based biometric parameter measurement submodule. In this illustration, a sequential wavefront sensor 502 is attached to a surgical microscope 500, and an OCT based eye biometric parameter measurement submodule 510 as well as an eye camera 508 is integrated with the wavefront sensor 502.

The surgical microscope has its own objective lens 501. A main beam splitter 561 is positioned below the objective lens 501 to separate and combine visible and infrared light beams. The main beam splitter 561 is transmissive to visible light meant for the microscope 500 and is reflective to near infrared light meant for the wavefront sensor and the camera as well as the biometric parameter measurement submodule. A shield window or shield lens 552 is arranged below the beam splitter 561 and a number flood illumination light sources (such as LEDs) are arranged around the shield to provide flood illumination to the patient eye for the camera to capture a live eye image.

The wavefront sensor module 502 comprises two 4-F relay stages with its light path folded to relay the wavefront from the corneal or pupil plane of a patient eye 599 to a wavefront sampling aperture 518. The first relay stage comprises a first lens 554 and a second lens 516 and relays the wavefront (with certain optical magnification or demagnification depending on the focal length of the first and second lens) from the corneal or pupil plane to an intermediate image plane where a dynamic transmissive focus variable lens 578 is disposed. This focus variable lens can be used to partially or fully compensate the sphere component of the wavefront or to dynamically change its focus to enable a scanning of the sphere component of the wavefront.

The second relay stage comprises a third lens 540 and a fourth lens 542 and further relays the wavefront from the intermediate plane (where the dynamic transmissive focus variable lens 578 is disposed) to the final wavefront sampling aperture 518 plane. A mega-aperture 577 can be arranged at the first Fourier transform plane to prevent light outside a certain diopter range from entering the rest of the wavefront relay path. A band pass filter 576 can also be arranged in the second relay stage to reject light outside an intended wavefront sensing spectral range from entering the rest of the wavefront relay light path. A MEMS (microelectrical mechanical system) mirror 512 folds the beam path and scans the wavefront sequentially around the aperture 518 so that different sub-wavefronts are sampled. A sub-wavefront focusing lens 520 is positioned next to the sample aperture 518 to focus the sampled sub-wavefronts to a position sensing device 522. A diffuser (not shown in FIG. 5B) can be arranged in front of the position sensing device 522 to ensure a certain light spot size on position sensing device 522.

The OCT based biometric parameter measurement submodule 510 can be based on an optical fiber low coherence interferometer. Light from a low coherence light source (such as a fiber pigtailed superluminescent diode or SLD) 572 is directed to a directional coupler 590 and is split into a sample arm 588 and a reference arm 592. The reference arm can have a fiber coil that ensures an overall reference optical path length approximately matched to that of the sample arm. Light in the sample arm can be collimated and/or focused and/or scanned. Lens 586, scanner 582, lens 584 and scanner 580 are just some exemplary possibilities in terms of manipulating/scanning the sample beam. The sample light beam is sent to a patient eye through a polarization beam splitter (PBS) 574. Sample light wave returned from the eye (especially by all the eye optical interfaces) that has the original polarization can be collected by the same sample arm optics to recombine with the light wave from the reference arm to create optical low coherence interference and then sent to a detector or a detection module 594 for signal extraction. Sample light from the eye having an orthogonal polarization will be reflected by the PBS 574 to be directed to the wavefront sensor module for wavefront or refraction measurement.

The eye camera module 508 comprises a camera lens 568 and an image sensor 562. The camera lens 568 can be designed to work in combination with the first lens 554 to form an eye anterior image on the image sensor 562. An imaging beam splitter 560 can be arranged to reflect light of the flood light spectral band meant for live eye camera imaging to the eye camera module 508. The spectral band of the SLD can be selected to be different such that light in that spectral band will pass through the beam splitter 560 and be channeled to the rest of the wavefront sensing path.

Note that the wavefront sensor as illustrated in FIGS. 5A and 5B does not have to be a sequential wavefront sensor, it can be any refraction measurement device. The eye biometric parameter measurement device or submodule does not need to be limited to an OCT or OLCR, it can be a scheimpflug camera or even a nuclear magnetic resonance imaging module. The spectral band used for wavefront sensing does not need to be the same as the one used for biometric parameter measurement. In such a case, a WDM (wavelength division multiplexing) fiber coupler can be used to combine and split the two spectral bands of light.

Although auto-detection of the phase of an eye under a cataract surgery is desired, at this moment, it should also be noted that another embodiment of the present disclosure is to allow the surgeon to manually select or interrupt to select the phase so that it can be ensured that the refraction value used for IOL calculation is that from the aphakic phase.

Note also that as still another embodiment, the digital processor 504 can be configured to combine the information provided by either the pre-op biometry and/or refraction data or the intra-op refraction data or the intra-op Purkinje image data or the intra-op biometry data to determine the phase of a cataract surgery.

With the automatic detection of the cataract surgical phase of an eye, the digital processor can be further configured to only display refraction histogram in the phakic phase and pseudo-phakic phases, and to only display IOL power histogram in the aphakic phase or to display both refraction histogram and IOL power histogram in the aphakic phase.

Figure 6:
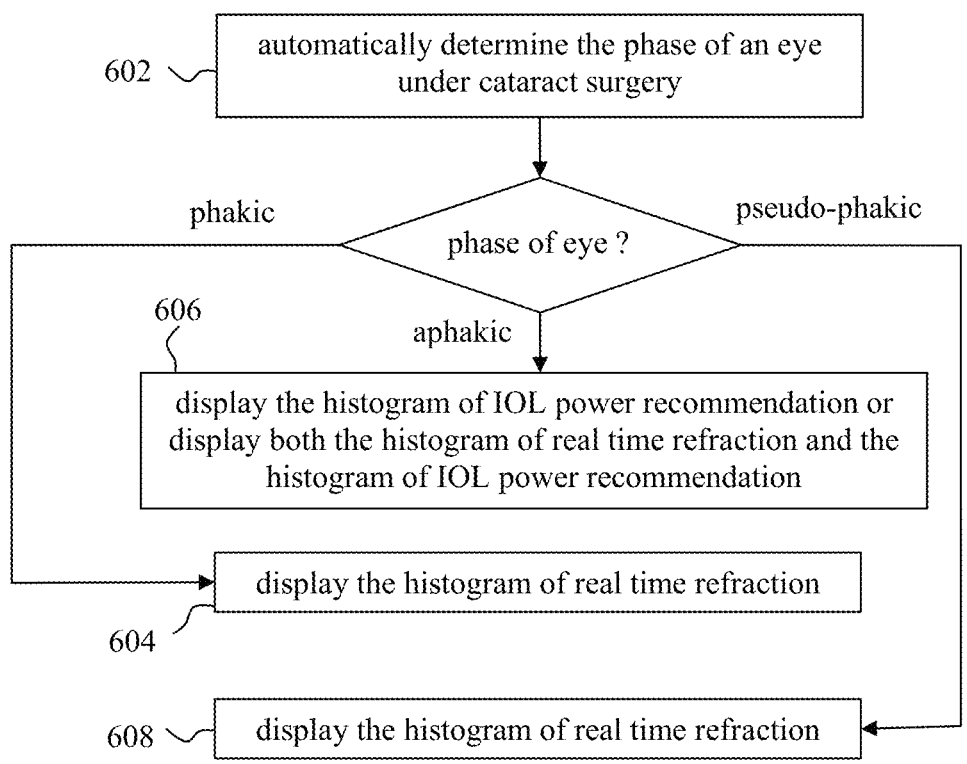
FIG. 6 shows the major steps involved in one embodiment to meaningfully and automatically display either a histogram of live refraction or a histogram of IOL power recommendation or both depending on the cataract surgical phase.

FIG. 6 shows the major steps involved in one embodiment to meaningfully and automatically display either a histogram of intra-operative refraction or a histogram of IOL power recommendation or both. The first step 602 is to automatically determine the phase of an eye under cataract surgery. If the eye is phakic, the next step 604 is to display the histogram of intra-operative refraction in the phakic phase. If the eye is aphakic, the next step 606 is to display the histogram of IOL power recommendation or to display both the histogram of refraction and the histogram of IOL power recommendation. If the eye is pseudo-phakic, the next step 608 is to display the histogram of intra-operative refraction in the pseudo-phakic phase.

As another embodiment of the present disclosure, a confidence level of intra-operative refraction data is calculated and displayed in real time. As will be explained in more detail shortly, the confidence level value can be calculated based on an algorithm that takes into account different qualifiers, including alignment of the eye, wavefront signal strength, the optical energy or power distribution among all sampled sub-wavefronts, the overall average prismatic tilt of all the sampled sub-wavefronts, the amount of higher order aberrations, etc. In one embodiment, the confidence value is associated with the most recent qualified refraction.

In terms of displaying the confidence level or value in real time, one embodiment is to display it as a height or length varying percentage bar; another embodiment is to correlate the confidence percentage value to a color from a rainbow spectrum with the confidence percentage indicator (such as the word "Rx" or the numerical value that shows the refraction) being shown in different colors. In this latter case, the confidence value can be digitized such that for a certain real time refraction that falls within a certain digitized confidence level range, a certain color is assigned to the real time refraction and is displayed to the surgeon.

Figure 7:
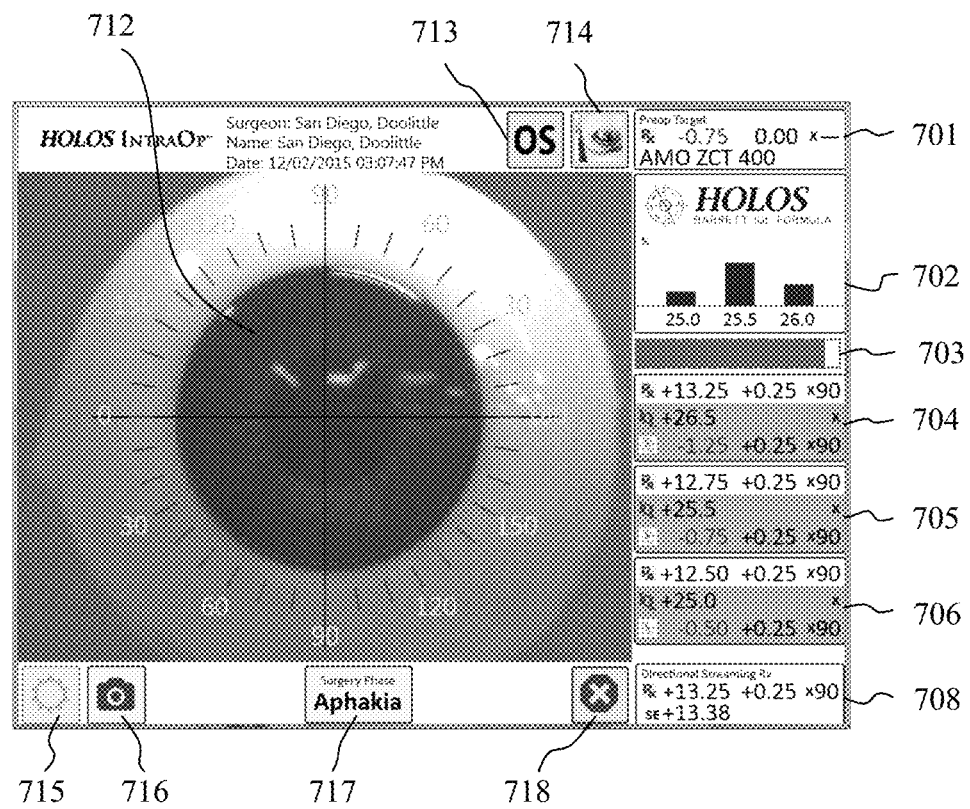
FIG. 7 shows an example display similar to that of FIG. 4 but with a confidence percentage bar.

FIG. 7 is an example live display in which a confidence percentage bar 703 is shown in addition to those pieces of information shown in FIG. 4. Note that the confidence percentage bar can be arranged anywhere on the live display but is preferred to be next to the current qualified refraction or current IOL power recommendation. In FIG. 7, the confidence percentage bar 703 is below the histogram 702 and above the most recent qualified refraction. Note that in the aphakic phase, as there is a correspondence between a qualified refraction and an associated IOL power recommendation, therefore, the confidence percentage is also a confidence value for the current IOL power recommendation.

As an alternative, in another embodiment, instead of showing the confidence percentage of the current refraction, the confidence percentage shown can also be that associated with the refraction that has the highest occurrence frequency (i.e. the one having the highest value in the refraction histogram or the one having the highest value in the IOL power histogram). In addition, the confidence percentage bar can also be color coded such that one or more threshold(s) can be established to indicate to a surgeon if the confidence level is high or medium or low. For example, when the confidence value is above 90%, the confidence bar can be in green color, when the confidence value is between 75% and 90%, the confidence bar color can be yellow, when the confidence value is between 50% and 75%, the color of the confidence bar can be orange, and when the confidence value is below 50%, the color can be grey. These color codings can be configured per a surgeon's personalized preference as well. Similar color coding can also be applied to the font color of the refraction and/or IOL power and/or expected final pseudo-phakic refraction values.

In terms of calculating the overall confidence level value, we can assume that the thresholds for different qualifiers have been established and that the refraction data being processed have passed all the qualification thresholds. Then for each qualifier, a range can be defined between a practical good case and a threshold case and a confidence percentage value can be assigned to each qualifier or qualification parameter within the range. The overall confidence level can then be defined as a function of each individual qualifier confidence percentage values such as the average.

For example, consider that the degree of eye alignment relative to the refraction measurement device is a qualifier. From a practical point of view, when the eye is aligned to within ±0.1 mm of the optical axis of the eye refraction measurement device, the confidence level can be considered as 100%. Assume that the qualification threshold is established as when the eye is aligned to within ±0.5 mm of the device optical axis and the corresponding confidence level for this threshold case is 0%. Then for an arbitrary eye alignment that is between the ±0.1 mm case and the ±0.5 mm threshold case, the confidence percentage value can be assumed to be linear or non-linear. In the linear case, if the eye center is 0.2 mm away from the optical axis, the corresponding eye alignment confidence level will be 75% (0.2 mm is three quarter from 0.5 mm over the range between 0.1 mm and 0.5 mm).

Similarly, if the uniformity of optical energy or power distribution among all sampled sub-wavefronts is another qualifier. Then from a practical point of view, when the uniformity ratio (standard deviation divided by the average) is 2%, the uniformity confidence level can be considered 100%. If the uniformity ratio threshold is 6% which corresponds to a uniformity confidence level of 0%, then assuming a linear relationship, a uniformity ratio of, say, 3% will result in a uniformity confidence percentage value of 75% (3% is three quarter away from 6% over the range between 2% and 6%).

We can propagate the same argument to one more qualifier, the average prismatic tilt of the overall wavefront. From a practical point of view, when the average prismatic tilt of the overall wavefront is within 1 degree relative to the optical axis of the refraction measurement device, the confidence level can be considered as 100%. Assuming that the threshold is 11 degree which corresponds to a confidence value of 0%, then for an arbitrary average prismatic tilt of 4 degree, under the assumption of a linear relationship, the corresponding confidence level will be 70% (4 degree is 70% away from 11 degree over the range between 1 degree and 11 degree).

Similar calculations can be applied to other qualifiers, including overall wavefront signal strength, frame to frame refraction difference, and the amount of higher order aberrations, etc. An overall confidence level can be defined as the average of all the individual confidence levels. The overall confidence level can also be defined with different weighting factors depending on the importance of a particular qualifier.

Note that there are many other ways to calculate the confidence level associated with each qualifier and non-linear relationship can be established across the range between a practically good enough case and a threshold case. For example, instead of using a linear relationship across the range, a non-linear relationship such as a square root relationship can be employed. In such as case, a 75% confidence level in the linear relationship case will be equal to SQRT(75%)=86.6% in the non-linear relationship case, and a 36% confidence level in the linear relationship case will be equal to SQRT(36%)=60% in the non-linear relationship case.

Meanwhile, the overall confidence level can also be non-linear in terms of its association with different qualifier's confidence levels. For example, some qualifiers, like the alignment of the eye and the overall prismatic tilt in the aphakic phase can have a higher weighting as compared to other qualifiers such as the amount of higher order aberrations. Therefore, above shown method to calculate the confidence level is only exemplary.

In addition, there can also be a combined consideration of the confidence level and the steadiness of a qualified refraction. One embodiment of the disclosure is to combine the calculation of the occurrence frequency distribution of qualified refractions with the confidence of the corresponding refractions to produce a combined confidence weighted histogram and to display this confidence weighted histogram to a surgeon in real time. Note that in such a case, the modified histogram can show a digitized refraction that is the tallest in the histogram but the refraction may not have the highest occurrence frequency simply because it may have a high confidence level that has been weighted and factored in the histogram. Accordingly, the recommended IOL power can also be modified to factor in the calculation of the occurrence frequency distribution of IOL power and the confidence level associated with that IOL power, and to produce a combined confidence weighted histogram of IOL power recommendation.

Note that these modifications to the histogram can also be optimized over time through regression. Artificial intelligence or neural network can be built in an algorithm for a particular surgeon to automatically adjust the weighting factors of different qualifiers using clinical data collected over a large number of patients and to produce an optimized weighting function that will produce a statistically optimized real time refraction or real time IOL power recommendation, thus leading to a statistically optimized surgical outcome for that particular surgeon.

Note also that all additional features and embodiment variations as mentioned in the refraction and IOL recommendation histogram examples can be applied to the confidence weighted refraction and/or confidence weighted IOL power recommendation cases. For example, automatic detection of the phase of an eye under a cataract surgery can be implemented to determine if a confidence weighted refraction histogram should be displayed (like in phakia and pseudo-phakia) or an associated confidence weighted IOL power recommendation histogram should be displayed (like in aphakia).

In addition, in the aphakic phase, the confidence weighted refraction histogram can also be used to automatically select the most likely "true" aphakic refraction and this selected aphakic refraction can be used to calculate an IOL power using a regression formula that also takes into consideration the biometry data collected pre- or intra-operatively as well as the statistical data collected over a large number of patients. In practice, once a surgeon has conditioned an aphakic eye, and had the eye positioned steady and aligned, overtime, this recommended IOL power will be continuously updated on the display and will gradually become steady to give the surgeon higher confidence in picking the power of an IOL to be implanted.

Note also that the discussion we have had in regard to the power of an IOL can be extended to and should be considered to be extendable to the case of a toric IOL in which the power of the IOL refers to the both the sphere and the cylinder instead of just the sphere of a monofocal IOL. In addition, the extension should also be applied to the selection of more advanced IOLs including extended depth of focus IOLs, bi-focal or tri-focal or multi-focal IOLs, accommodating IOLs (AIOL) and even recommendation of LRI (limbal relaxing incision) or CRI (corneal relaxing incision) in terms of the position and/or direction of the incision and the length of the incision. In other words, the refraction or IOL power recommendation produced by the artificial intelligence of the presently disclosed means can be used to prescribe not only the sphere but also the cylinder and cylinder axis for a refraction procedure. Moreover, since the device being disclosed to measure the optical refraction property of a patient eye is not limited to an auto-refractor but should include a wavefront sensor as well as one or more optical biometry measurement devices, the disclosure should therefore be considered as including higher order aberrations and hence the prescription as exemplified in terms of IOL power recommendation etc. can also be extended to include prescription in correcting higher order aberrations such as coma, trefoil and spherical aberration.

In addition, as one embodiment of the present disclosure, the digital processor can also be configured to store stabilized prescriptions or IOL power recommendations or histogram(s) obtained while the eye is aligned and to keep some of those prescriptions still displayed for a predefined time period even after the eye is moved away from alignment.

In addition, in further embodiments of the present disclosure, the display of information can be configured such that any one of: the real time image of the subject eye; the histogram of occurrence frequency distribution of the qualified refraction values, and/or a histogram of occurrence frequency distribution of IOL powers predicted based on an IOL predictive algorithm that incorporates among other parameters the aphakic refraction of the patient eye in one or more of the phakic, aphakic, or pseudo-phakic phase of the vision correction procedure; the indication of the phase of the vision correction procedure, displaying the pre-operatively determined target refraction value; the one or more of most recent qualified intra-operative refraction values; and sampled wavefronts having overall signal strength higher than one threshold value and/or lower than another threshold value can be displayed in any one of a first portion of the display screen, a second portion of the display screen, a third portion of the display screen, a fourth portion of the display screen, a fifth portion of the display screen, and/or a sixth portion of the display screen.

Although various embodiments that incorporate the teachings of the present invention have been shown and described in detail herein, those skilled in the art can readily devise many other varied embodiments that still incorporate these teachings.

What is claimed is:

1. A method for real time detection and measurement of aberration values of a wavefront returned from a subject eye, wherein the method is adapted to be performed while a surgical procedure on a subject eye is ongoing, with the method performed by a computer system coupled to receive wavefront aberration values from a wavefront sensor configured to measure real time aberration values of a wavefront returned from the eye of a subject while an image of the subject eye is being viewed by an operator during an ongoing vision correction procedure, coupled to receive pre- or intra-operative biometric measurements of the subject eye being viewed by an operator during the ongoing vision correction procedure from a biometric parameter measurement module, and coupled to a display, the method comprising:

disqualifying unreliable measured real time aberration measurements received from the wavefront sensor based on qualifying parameters including one or more of eye alignment measurements, wavefront power measurements, high-order aberration measurements, prismatic wavefront tilt, and inter-frame wavefront steadiness to collect a set of qualified real time aberration values;

calculating and storing qualified intra-operative refraction values of the subject eye based on qualified wavefront measurements;

recording the occurrence frequency of stored qualified refraction values of the subject eye;

intra-operatively detecting whether the patient eye is in the phakic, aphakic, or pseudo-phakic phase of the vision correction procedure in real time based on the difference between pre-operative predicted values of refraction power and measured intra-operative phakic, aphakic, or pseudo-phakic values of refraction power of the subject eye;

displaying a real time image of the subject eye, a histogram of occurrence frequency distribution of the qualified refraction values, and/or a histogram of occurrence frequency distribution of IOL powers predicted based on an IOL predictive algorithm that incorporates among other parameters the aphakic refraction of the subject eye in one or more of the phakic, aphakic, or pseudo-phakic phase of the vision correction procedure, an indication of the phase of the vision correction procedure, a pre-operatively determined target refraction value, and one or more of most recent qualified intra-operative refraction values.

2. The method of claim 1 where calculating and storing qualified intra-operative refraction values further comprises:

receiving pre- or intra-operatively measured anatomical parameters of the subject eye including one or more of axial length, anterior chamber depth, corneal anterior (K or keratometry values) and/or posterior profiles, corneal steep meridian and flat meridian axis and power, corneal astigmatism, cornea thickness, aqueous depth, lens thickness, lens anterior and posterior profile, pupil size or diameter, pupil center, white to white distance, iris center, and retina thickness; and predicting required IOL power based on measured aphakic optical power of the subject eye and one or more of the pre- or intra-operatively measured anatomical parameters.

3. The method of claim 1 where disqualifying comprises: disqualifying sampled wavefronts having non-uniform optical power.

4. The method of claim 1 where disqualifying comprises: disqualifying sampled wavefronts having high amount of higher order aberrations.

5. The method of claim 1 where disqualifying comprises: disqualifying sampled wavefronts having a prismatic tilt value higher than a threshold value.

6. The method of claim 1 where disqualifying comprises: disqualifying sampled wavefronts having overall signal strength higher than one threshold value or lower than another threshold value.

7. The method of claim 1 where disqualifying comprises: disqualifying sampled wavefronts having inter-frame variation in refraction value above a threshold.

8. The method of claim 1 further comprising: assigning an overall confidence value to a qualified wavefront measurement by applying threshold values to one or more qualifying parameters to determine confidence values of individual qualifying parameters and combining the confidence values for each qualifying parameter; and
displaying an indication of the overall confidence value of the most recently measured intra-operative refraction value on the display screen.

9. The method of claim 8 where assigning an overall confidence value comprises:
assigning a confidence value which depends on variation of eye alignment with an optical axis of the wavefront sensor.

10. The method of claim 8 where assigning an overall confidence value comprises:
assigning a confidence value which depends on variation of power distribution between sampled wavefronts.

11. The method of claim 8 where assigning an overall confidence value comprises:
assigning a confidence value which depends on variation of the average prismatic tilt of all sampled wavefronts.

12. The method of claim 1 where intra-operatively detecting whether the subject eye is in the phakic, aphakic, or pseudo-phakic phase of the vision correction procedure comprises:
indicating that the subject eye is in the phakic phase of the vision correction procedure if a pre-operative predicted value of phakic refraction power is within a range selectable by an end user from ±0.5 to ±4.0 diopters of an intra-operatively measured value of refraction power of the patient eye.

13. The method of claim 1 where intra-operatively detecting whether the subject eye is in the phakic, aphakic, or pseudo-phakic phase of the vision correction procedure comprises:
indicating that the subject eye is in the aphakic phase of the vision correction procedure if a pre-operative predicted value of aphakic refraction power is within a range selectable by an end user from ±0.5 to ±4.0 diopters of an intra-operatively measured value of refraction power of the patient eye.

14. The method of claim 1 where intra-operatively detecting whether the subject eye is in the phakic, aphakic, or pseudo-phakic phase of the vision correction procedure comprises:
indicating that the subject eye is in the pseudo-phakic phase of the vision correction procedure if a pre-operative predicted value of pseudo-phakic refraction power is within a range selectable by an end user from ±0.5 to ±4.0 diopters of an intra-operatively measured value of refraction power of the patient eye.

15. The method of claim 1 wherein displaying the real time image of the subject eye is in a first portion of the display screen, displaying the histogram of occurrence frequency distribution of the qualified refraction values, and/or a histogram of occurrence frequency distribution of IOL powers predicted based on an IOL predictive algorithm that incorporates among other parameters the aphakic refraction of the patient eye in one or more of the phakic, aphakic, or pseudo-phakic phase of the vision correction procedure is in a second portion of the display screen, displaying the indication of the phase of the vision correction procedure is in a third portion of the display screen, displaying the pre-operatively determined target refraction value is in a fourth portion of the display screen, and displaying the one or more of most recent qualified intra-operative refraction values is in a fifth portion of the display screen.

* * * * *